United States Patent [19]
Eng

[11] Patent Number: 6,081,328
[45] Date of Patent: Jun. 27, 2000

[54] ENHANCEMENT OF RAMAN SCATTERING INTENSITY OF THIN FILM CONTAMINANTS ON SUBSTRATES

[75] Inventor: Frederick P. Eng, San Jose, Calif.

[73] Assignee: International Business Machines Corporation, Armonk, N.Y.

[21] Appl. No.: 09/357,509

[22] Filed: Jul. 20, 1999

[51] Int. Cl.$^7$ .............................. G01J 3/44; G01N 21/65
[52] U.S. Cl. ............................................................ 356/301
[58] Field of Search ............................................. 356/301

[56] References Cited

U.S. PATENT DOCUMENTS

| | | | |
|---|---|---|---|
| 5,693,152 | 12/1997 | Carron | 356/301 |
| 5,828,450 | 10/1998 | Dou et al. | 356/301 |
| 5,864,397 | 1/1999 | Vo-Dinh | 356/301 |
| 5,869,346 | 2/1999 | Xiaoming et al. | 356/301 |

OTHER PUBLICATIONS

Scheuler, P.A., et al., Physical Structure, Optical Resonance, and Surface–Enhanced Raman Scattering of Silver–Island Fioms on Suspended Polymer Latex Particles, Analytical Chemistry v. 65 n 22 Nov. 15, 1993, pp. 3177–3186.

Hua Zhong Yu, et al., "Surface Enhanced Raman Scattering (SERS) from Azobenzene Self Assembled 'Sandwiches'", Langmuir (USA) vol. 15, No. 1 Jan. 5, 1999 pp. 16–19.

*Primary Examiner*—F. L. Evans
*Attorney, Agent, or Firm*—Robert O. Guillot

[57] ABSTRACT

In the present invention the enhanced Raman spectra of a substance is obtained by depositing a metallic layer upon the surface of the substance. The Raman spectrographic laser is directed to and through the metallic layer, and the Raman scattered energy passes back through the metallic layer and is analyzed by the spectrographic detector. The metallic layer is therefore thin enough to permit passage of the laser energy and scattered energy without significant attenuation. In a preferred embodiment, the spectrographic laser is an argon ion laser and the metallic layer is composed of silver with a thickness of from approximately 1 nm to approximately 20 nm. The present invention is particularly adapted for the analysis of thin film smears deposed upon substrates, such as hard disks. In this application a smear having a thickness of approximately several nm to 30 nm is analyzed by depositing a metallic layer on the smear having a thickness of from approximately 1 nm to approximately 20 nm, and preferably approximately 1 to 8 nm. The preferred metallic layer deposition method is to deposit the metal in a plurality of islands having a diameter from approximately 50 $\mu$m to approximately 60 $\mu$m. The enhanced Raman spectrographic method of the present invention is thus suitable for identifying contaminating smears on the surface of substrates, as well as providing spectrographic information regarding substrate surfaces upon which the thin film metallic layer is deposited.

21 Claims, 3 Drawing Sheets

ENHANCEMENT OF RAMAN SCATTERING INTENSITY OF THIN FILM CONTAMINANTS ON SUBSTRATES

BACKGROUND OF THE INVENTION

1. Field of the Invention

The present invention relates generally to Raman spectroscopy, and more particularly to methods for obtaining enhanced Raman spectra signal intensity from thin film contaminants on a substrate surface.

2. Description of the Prior Art

Unwanted contamination on the surface of a substrate can adversely affect operational and manufacturing processes that depend upon a clean substrate surface. For instance, where unwanted contamination is disposed on a hard disk surface, or on the surface of a read/write head, the signal to noise ratio (S/N) can be adversely affected, and where the surface contamination is particularly severe, a head crash can occur which can destroy a hard disk drive. Given the continually shrinking head/disk interface tolerances, contamination by thin films of nanometer level thickness can create substantial problems; such contaminating thin films are termed smears and often are the result of contamination during one or more steps in the disk or head manufacturing process or handling subsequent to manufacturing. Many of such smears are comprised of organic polymers that exist on the surface of a manufactured hard disk.

A typical smear contamination problem arises during the read/write testing or use of a completed hard disk, where the smear causes a significant signal loss in the contaminated area. It is then important to analyze the smear to determine its composition, because it is often possible to then identify the manufacturing or handling step in which the contamination occurred and thereafter take steps to eliminate the source of the contamination. The throughput of acceptable product can therefore be improved.

A standard technique for the analysis of smears is Raman spectroscopy through which the smear composition can be determined. However, a limitation on the use of standard Raman spectroscopy is the need for a sample that has sufficient thickness to create a scattered signal with sufficient intensity for detection above the background noise. Significantly, where a smear on a hard disk has a thickness on the order of approximately several nanometers or more, it will cause substantial signal degradation; however, the smear thickness is oftentimes insufficient to provide a detectable signal for standard Raman spectrographic analysis. A problem therefore exists in the analysis of thin film smears in order to identify them and thereafter improve manufacturing throughput.

Techniques for surface enhanced Raman spectroscopy exist in the prior art. Such techniques involve the utilization of a metal surface on which a thin film smear is disposed. Where the laser irradiates the smear an enhanced Raman scattering signal is generated. This technique, termed surface enhanced Raman spectroscopy (SERS) is utilizable where the smear is disposed upon a metal substrate, such that the smear is directly irradiated by the laser. However, where the smear is already disposed upon a substrate, such as a hard disk surface, it is not possible to place the smear upon a metal substrate surface, such that the smear can be irradiated by the spectroscopic laser.

A need therefore exists for a method for the analysis of thin film smears that are disposed upon a substrate surface, and particularly a method for obtaining an enhanced Raman scattering spectra signal.

SUMMARY OF THE INVENTION

In the present invention the enhanced Raman spectra of a substance is obtained by depositing a metallic layer upon the surface of the substance. The Raman spectrographic laser is directed to and through the metallic layer, and the Raman scattered energy passes back through the metallic layer and is analyzed by the spectrographic detector. The metallic layer is therefore thin enough to permit passage of the laser energy and scattered energy without significant attenuation. In a preferred embodiment, the spectrographic laser is an argon ion laser and the metallic layer is composed of silver with a thickness of from approximately 1 nm to approximately 20 nm. The present invention is particularly adapted for the analysis of thin film smears deposed upon substrates, such as hard disks. In this application a smear having a thickness of approximately several nm to 30 nm is analyzed by depositing a metallic layer on the smear having a thickness of from approximately 1 nm to approximately 20 nm, and preferably approximately 1 to 8 nm. The preferred metallic layer deposition method is to deposit the metal in a plurality of islands having a diameter from approximately 50 $\mu$m to approximately 60 $\mu$m. The enhanced Raman spectrographic method of the present invention is thus suitable for identifying contaminating smears on the surface of substrates, as well as providing spectrographic information regarding substrate surfaces upon which the thin film metallic layer is deposited.

It is an advantage of the present invention that a method for obtaining enhanced Raman spectra of a surface is provided.

It is another advantage of the present invention that a method for providing enhanced Raman spectra of smears disposed on substrate surfaces is provided.

It is a further advantage of the present invention that a method for identifying thin film smears on hard disks is provided.

It is yet another advantage of the present invention that a method for improving the manufacturing process for a substrate is provided.

It is yet a further advantage of the present invention that a method for identifying thin film smears on hard disk surfaces is provided, such that the manufacturing step in which the thin film smear occurred can be identified and the cause of the smear can be eliminated.

These and other objects and advantages of the present invention will be understood by those skilled in the art upon reviewing the following detailed description which makes reference to the several figures of the drawings.

IN THE DRAWINGS

DETAILED DESCRIPTION OF THE PREFERRED EMBODIMENTS

The present invention is a method for improving the signal to noise ratio (S/N ratio) of the Raman scattering spectra from a thin film smear disposed upon a substrate. Such a substrate may be the surface of a hard disk, the surface of a read/write head, or almost any substrate surface on which a thin film smear exists.

Figure 1:
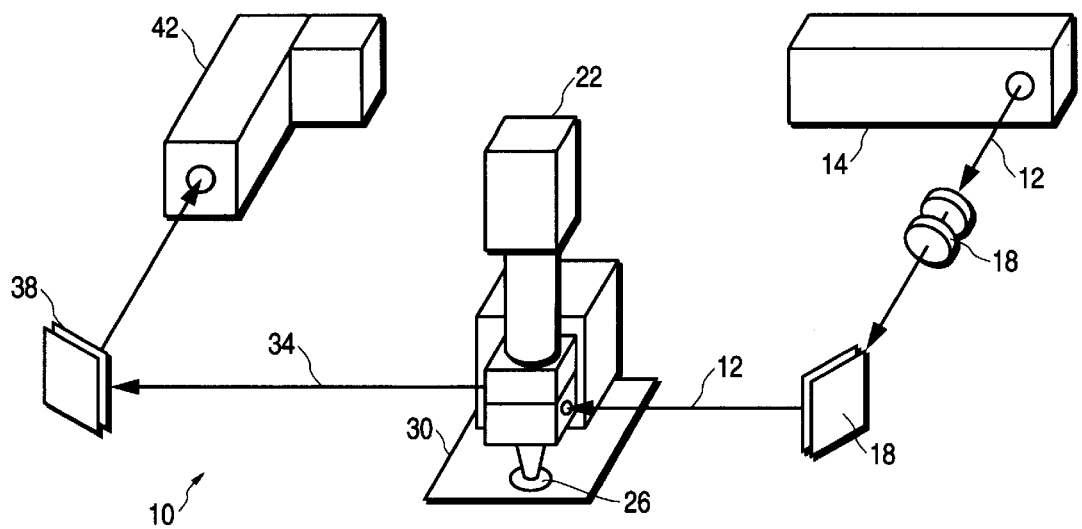
FIG. 1 is a schematic diagram of a standard Raman spectrographic system.

A standard Raman spectrograph 10 is schematically depicted in FIG. 1, wherein a laser light beam 12 from a laser source 14 is directed through optical components 18 to a microscope 22 for directing the laser beam energy onto a specimen 26 disposed upon the stage 30 of the microscope 22. Scattered laser light 34 from the sample passes back through the microscope, through further optical components 38 to a spectrographic detector 42 which determines the intensity of the Raman scattered light spectra.

A significant feature of the present invention is the discovery that a surface treatment upon the smear prior to laser exposure can enhance the signal (improve the S/N ratio) from the sample. Specifically, an enhanced S/N ratio is achieved in the present invention by depositing a thin metallic film on top of the smear prior to Raman scattering analysis of the smear as is next discussed.

Figure 2:
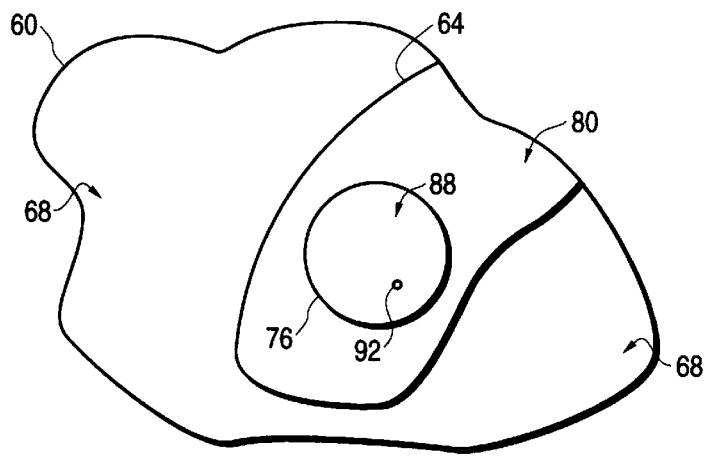
FIG. 2 is a top plan view of a substrate having a smear disposed thereon and having a thin film metallic layer disposed upon the smear.
Figure 3:
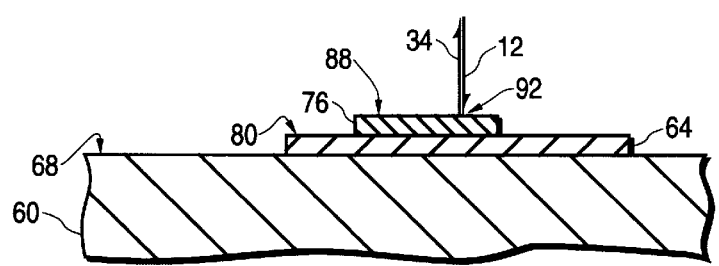
FIG. 3 is a cross-sectional view of the substrate depicted in FIG. 2, taken along lines 3—3 of FIG. 2.

FIG. 2 is a top plan view of a substrate 60 having a smear 64 disposed on the substrate's surface 68, with a metallic layer 76 disposed on the surface 80 of the smear 64, and FIG. 3 is a side cross-sectional view taken along lines 3—3 of FIG. 2. As depicted in FIGS. 2 and 3, a substrate 60 has a contaminating smear 64 disposed on its upper surface 68. The smear 64 may have a thickness of approximately several nm to approximately 30 nm. Such a smear thickness is too thin for standard Raman spectrographic analysis. To enhance the scattered signal, a thin film metallic layer 76 is deposited upon upper surface 80 of the smear. The composition of the metallic layer and its thickness is determined primarily based upon the type of laser 14 utilized in the Raman spectrograph 10. In the preferred embodiment described in the examples herebelow, a green argon ion laser having a wavelength of 514 nm is utilized and the thin film metallic layer 76 is composed of silver. In other applications, metallic layers 76 composed of gold, copper or nickel can be suitable, and these metals appear to be preferable with a longer wavelength laser, such as a 647 nm laser. In the examples of the preferred embodiment, the silver layer 76 is deposited as a plurality of areas or islands 88 having a diameter of approximately 50–60 µm and a thickness of approximately 8 nm. The silver islands 88 are preferably deposited utilizing a sputtering system such as a vacuum evaporation system. The laser beam 12 is focused to a spot 92 having a diameter of approximately 1.5 µm.

It is therefore to be understood that a substrate having a contaminant smear is selected for analysis to determine the composition of the smear. Such a substrate may be a hard disk with a thin film smear disposed thereon, such that a signal loss occurs in the area of the disk surface covered by the smear. A portion of the substrate, such as a half inch diameter disk specimen is taken from the substrate and a plurality of silver islands are sputter deposited upon it. Thereafter, the test specimen 26 is placed in the Raman spectrograph and analyzed. The laser spot 92 is focused upon the metallic layer 76 and scattered light 34 is received and analyzed by the detector. The laser energy therefore passes through the metallic layer 76 and is scattered by the molecular components of the smear 64. The scattered light energy 34 passes again through the metallic layer 76 and thence through the microscope and detector optics to the spectrographic detector 42. Therefore, the constraints on the thickness of the metallic layer 76 are such that it be thick enough to provide a continuous metal surface on top of the smear 64, and thin enough that the laser energy 12 and the scattered laser energy 34 not be overly attenuated by passage through the metallic layer 76. In the preferred embodiment a metallic layer thickness range of approximately 1 nm to approximately 20 nm appears suitable, and a thickness of approximately 1 nm to approximately 8 nm is preferred.

The present invention can therefore be described as reverse surface enhanced Raman spectroscopy (RSERS), as compared to standard surface enhanced Raman spectroscopy (SERS) known in the prior art. That is, in the SERS technique a smear is disposed upon a metal surface and the smear is directly illuminated by the laser and scattered light passes directly from the smear to the detector for analysis. In the RSERS system of the present invention the smear is not directly illuminated. Rather, the metallic surface is directed illuminated and the metallic layer thickness is such that the laser energy passes therethrough, is scattered by the smear molecular components, and the scattered light passes again through the metallic layer and is thereafter detected and analyzed. Specific examples of the RSERS method of the present invention are next provided.

Figure 4:
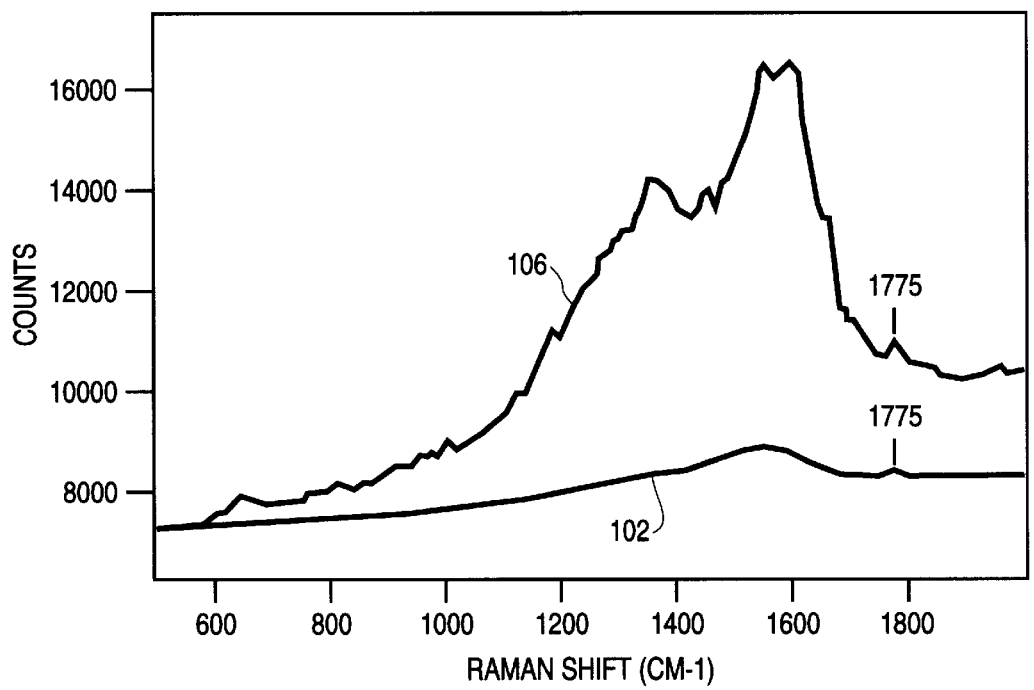
FIG. 4 depicts a Raman spectra from a first experiment utilizing the present invention.
Figure 5:
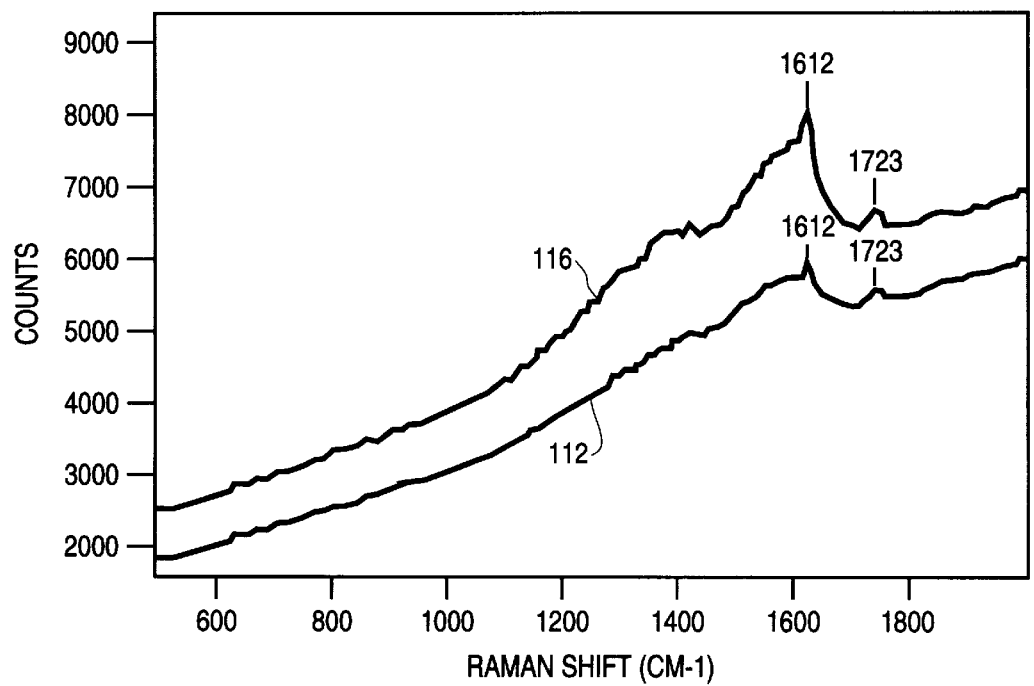
FIG. 5 depicts a Raman spectra from a second experiment utilizing the present invention.
Figure 6:
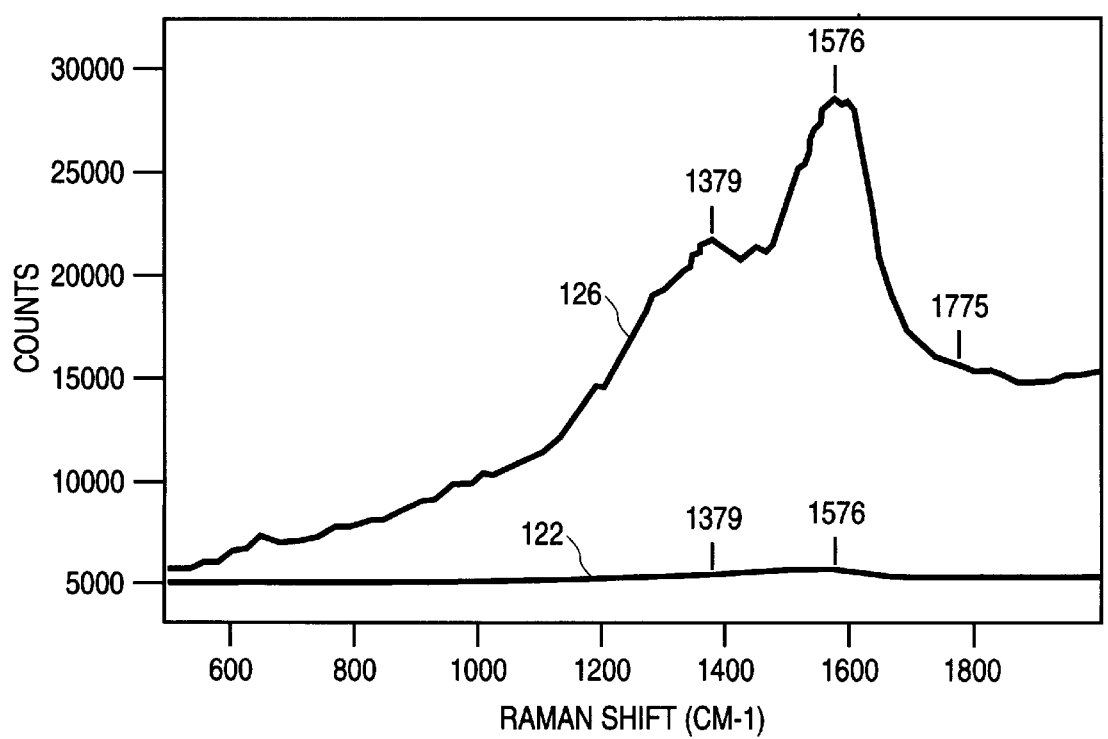
FIG. 6 depicts a Raman spectra from a third experiment utilizing the present invention.

Three experiments to demonstrate the effect of the thin film metallic layer were conducted, and the results are presented in FIGS. 4, 5 and 6. In each example a carbon-coated magnetic disk was used as the substrate. Raman spectroscopy was performed on a Renishaw Dual System 200 Raman spectrometer equipped with an integrated microscope (50× objective) and a Peltier cooled CCD detector. Spectra were collected using an argon ion laser having a 514 nm wavelength excitation at a power of 6 mW or less. Silver island film deposition was performed in a vacuum evaporator from Fullam Incorporated. The silver film islands were approximately 50–60 µm in diameter and approximately 8 nm in thickness.

In a first experiment, the results of which are presented in FIG. 4, the silver islands were deposited an Ultem (polyether imide) smear of approximately 4–6 µm in size and 30 nm in thickness. As depicted in FIG. 4, a signal enhancement of approximately 10× was observed for the Ultem smear based upon the characteristic carbonyl band at 1775 cm−1 between the standard Raman spectra line 102 before the silver film deposition and the (RSERS) Raman spectra line 106 after the silver film deposition of the present invention.

In the second experiment, the results of which are presented in FIG. 5, a polyethylene terephthalate (PET) smear of 4–6 µm in size and approximately 30 µm in thickness was deposited upon the carbon-coated hard disk substrate. A signal enhancement of approximately 3× is observed at the 1612 cm−1 band between the standard Raman spectra line 112 before silver film deposition and the RSERS Raman spectra line 116 after the silver film deposition of the present invention.

In a third experiment no smear was utilized. Rather, the silver thin film islands were deposited directly onto the carbon-coated hard disk substrate. As depicted in FIG. 6, a signal enhancement of 80× of the carbon overcoat, based on the intensity of the G (graphitic) band at 1576 cm−1 was observed between the standard Raman spectra line 122 before silver film deposition and the RSERS Raman spectra line 126 after the silver film deposition of the present invention. This example demonstrates a further application of the present invention in that it is not directed to the detection and identification of smears and their composition. Rather, the technique of the present invention provides enhanced information with regard to the characteristics of the carbon overcoat layer itself. This information can be useful because current technology seeks to provide hard disks with thinner carbon overcoats to improve signal strength from the magnetization layer while still acting as a protective barrier for the magnetization layer. Raman scattering according to the RSERS method of the present invention can therefore be utilized to provide information about the physical characteristics of the carbon overcoat layer. More generally, the RSERS method of the present invention provides enhanced Raman spectra signal intensity from the substance disposed beneath the metallic layer deposited in conformance with the present invention.

It is therefore to be understood that the RSERS method of the present invention provides enhanced Raman spectra for thin film contamination on a substrate. It can also provide information about the substrate surface itself, and generally the surface beneath the metallic layer. While the present invention has been described with reference to certain preferred embodiments, those skilled in the art will no doubt devise alterations and modifications thereto which may nevertheless include the true spirit and scope of the invention. It is therefore intended that the following claims cover all such alterations and modifications which fall within the scope of the claims.

What I claim is:

1. A method for providing enhanced Raman spectra from a substrate, comprising the steps of:

selecting a substrate for analysis, said substrate having a surface thereof;

depositing a metallic layer on said surface;

performing a Raman spectrographic analysis of said substrate by the steps of directing a laser beam through said metallic layer to said substrate and analyzing the Raman spectra of scattered laser beam energy that passes back through said metallic layer.

2. A method as described in claim 1 wherein said metallic layer is composed of a substance selected from the group consisting of silver, gold, copper and nickel.

3. A method as described in claim 2 wherein said metal is silver.

4. A method as described in claim 3 wherein said laser beam is generated by an argon ion laser.

5. A method as described in claim 1 wherein said metallic layer is deposited in discrete islands.

6. A method as described in claim 1 wherein said metallic layer is composed of silver and said metallic layer is deposited in islands.

7. A method as described in claim 6 wherein said metallic layer is deposited with a thickness of from approximately 1 nm to approximately 20 nm.

8. A method as described in claim 7 wherein said metallic layer is deposited in islands having an diameter of from approximately 50 $\mu$m to approximately 60 $\mu$m.

9. A method as described in claim 8 wherein said islands have a thickness of approximately 1 nm to approximately 8 nm.

10. A method as described in claim 8 wherein said islands have a thickness of approximately 8 nm.

11. A method for enhancing the Raman spectra of a thin film substance disposed on a substrate, comprising the steps of:

depositing a metallic layer upon said substance;

performing a Raman spectrographic analysis of said substance by the steps of directing a laser beam from a laser through said metallic layer into said substance, and analyzing scattered laser beam energy from said substance that passes back through said metallic layer.

12. A method as described in claim 11 wherein said metallic layer is composed of a substance selected from the group consisting of silver, gold, copper and nickel.

13. A method as described in claim 12 wherein said metal is silver.

14. A method as described in claim 13 wherein said laser is an argon ion laser.

15. A method as described in claim 11 wherein said metallic layer is deposited in discrete islands.

16. A method as described in claim 11 wherein said metallic layer is composed of silver and said metallic layer is deposited in islands.

17. A method as described in claim 16 wherein said metallic layer is deposited with a thickness of from approximately 1 nm to approximately 20 nm.

18. A method as described in claim 17 wherein said metallic layer is deposited in islands having an diameter of from approximately 50 $\mu$m to approximately 60 $\mu$m.

19. A method as described in claim 18 wherein said islands have a thickness of from approximately 1 nm to approximately 8 nm.

20. A method as described in claim 18 wherein said islands have a thickness of approximately 8 nm.

21. A method as described in claim 16 wherein said substance has a thickness from approximately several nm to approximately 30 nm.

* * * * *